United States Patent [19]

Tappe et al.

[11] 4,413,144
[45] Nov. 1, 1983

[54] 4-ISOPROPYL-4'-NITROBENZOPHENONE AND A PROCESS FOR THE PREPARATION OF 4'-NITROBENZOPHENONES SUBSTITUTED IN THE 4-POSITION

[75] Inventors: Horst Tappe, Dietzenbach; Herbert Wille, Frankfurt am Main, both of Fed. Rep. of Germany

[73] Assignee: Cassella Aktiengesellschaft, Frankfurt am Main, Fed. Rep. of Germany

[21] Appl. No.: 362,977

[22] Filed: Mar. 29, 1982

[30] Foreign Application Priority Data

May 25, 1981 [DE] Fed. Rep. of Germany ....... 3120747

[51] Int. Cl.³ ............................................. C07C 49/786
[52] U.S. Cl. ..................................... 568/306; 260/156
[58] Field of Search ......................... 568/306; 260/156

[56] References Cited

U.S. PATENT DOCUMENTS

| | | | |
|---|---|---|---|
| 2,561,190 | 7/1951 | Firestine | 568/306 X |
| 3,120,564 | 2/1964 | Milionis et al. | 568/306 X |
| 3,907,837 | 9/1975 | Effenberger et al. | 568/306 X |

*Primary Examiner*—Glennon H. Hollrah
*Assistant Examiner*—Vera C. Clarke
*Attorney, Agent, or Firm*—Connolly and Hutz

[57] ABSTRACT

4-Isopropyl-4'-nitrobenzophenone and other benzophenones of the formula

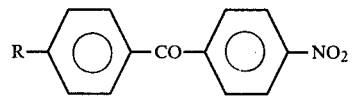

wherein R is hydrogen, alkyl having 1 to 20 carbon atoms, alkoxy having 1 to 20 carbon atoms, alkyl having 2 to 20 carbon atoms interrupted by oxygen, or alkoxy having 2 to 20 carbon atoms interrupted by oxygen, are prepared by reacting a substituted benzene compound of the formula

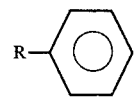

with p-nitrobenzoyl halide at temperatures of 10° to 140° C. in the presence of a Friedel-Crafts catalyst and an inert solvent which is an aliphatic hydrocarbon, a chlorinated aliphatic hydrocarbon or chlorinated aromatic hydrocarbon.

1 Claim, No Drawings

4-ISOPROPYL-4'-NITROBENZOPHENONE AND A PROCESS FOR THE PREPARATION OF 4'-NITROBENZOPHENONES SUBSTITUTED IN THE 4-POSITION

The present invention relates to 4-isopropyl-4'-nitrobenzophenone and a process for its preparation and for the preparation of other 4'-nitrobenzophenones substituted in the 4-position.

Aromatic ketones can be prepared by a Friedel-Crafts ketone synthesis in which an acylation component, as a rule a carboxylic acid halide, is reacted with an aromatic hydrocarbon in the presence of a catalyst (compare, for example, George A. Olah: Friedel-Crafts and Related Reactions, Volume III, Acylation and Related Reaction, Part 1 and 2, Interscience Publishers New York-London-Sydney (1964); Helv.Chim.Acta 41, 894 (1958); Angew. Chem. 84, 295 (1972); Synthesis (1978) 672).

The Friedel-Crafts ketone synthesis is carried out with an excess of the hydrocarbon or of the acid chloride, or nitrobenzene or carbon disulphide is used as a solvent. However, this method is of little value for an industrial synthesis since on the one hand an excess of one of the reactants, above all the hydrocarbon, produces to an increasing extent by-products and/or, on the other hand, the isolation of the ketones which as a rule are solid or have a very high boiling point is industrially elaborate and expensive.

Solvents, such as nitrobenzene or carbon disulphide, constitute very big industrial safety problems, so that their use is avoided as far as possible. In the case of carbon disulphide the problem is its ready flammability and its recovery, whilst nitrobenzene harbours not inconsiderable risks especially in the presence of aluminium chloride.

In addition, in some cases the yields are low or the final product desired has to be purified. Thus, for example, the reaction of tert.-butylbenzene, 4-nitrobenzoyl chloride and aluminium chloride produces a crude product from which the 4-tert.-butyl-4'-nitrobenzophenone desired has to be isolated by recrystallisation with a great effort. The yield is only 40% (J.Org. Chem. 31, 2708 (1966)).

It has now been found, surprisingly, that it is possible to synthesise 4-nitrobenzophenones substituted in the 4-position, in particular 4-isopropyl-4'-nitrobenzophenone, readily in high yields and high purities by a Friedel-Crafts ketone synthesis if the reaction is carried out at temperatures of 10° to 140° C. in an aliphatic hydrocarbon, or a chlorinated aliphatic or chlorinated aromatic hydrocarbon.

The process according to the invention for the preparation of benzophenones of the formula I

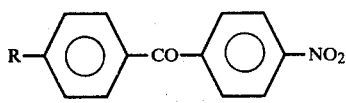

(I)

wherein R denotes hydrogen, an alkyl group having 1 to 20 C atoms or an alkoxy group having 1 to 20 C atoms, in which, if appropriate, the alkyl group or alkoxy group can be interrupted by oxygen, by reacting a compound of the formula II

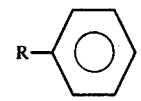

(II)

with a p-nitrobenzoyl halide in the presence of a Friedel-Crafts catalyst in an inert solvent, is characterised in that the reaction is carried out at temperatures of 10° to 140° C. in an aliphatic hydrocarbon, or a chlorinated aliphatic or chlorinated aromatic hydrocarbon.

This process is particularly suitable for the preparation of the new 4-isopropyl-4'-nitrobenzophenone. In this case, R in the formulae I and II denotes isopropyl.

In the formula I and II, an alkyl radical or alkoxy radical represented by R and, if appropriate, interrupted by oxygen can be straight-chain or branched and has in particular 1 to 6 C atoms.

Examples of suitable radicals R are methyl, ethyl, n-propyl, n-butyl, iso-butyl, tert.-butyl, n-pentyl, iso-pentyl, n-hexyl, isohexyl, ethoxy, n-propoxy, n-butoxy, n-pentoxy, n-hexoxy, ethoxyethoxy, n-propoxy-n-propoxy, ethoxyethyl and ethoxy-n-propyl. As already mentioned R is preferably isopropyl.

The p-nitrobenzoyl halide used can be, for example, p-nitrobenzoyl bromide or p-nitrobenzoyl chloride. p-Nitrobenzoyl chloride is preferred. The molar ratio between a compound of the formula II and the p-nitrobenzoyl halide is normally 1:(1 to 1.2), preferably 1:(1 to 1.05) in the reaction.

Examples of suitable aliphatic hydrocarbon solvents are aliphatic hydrocarbons having 6 to 16 C atoms (hexane to hexadecane) or mixtures thereof. The aliphatic hydrocarbon solvent used is as a rule a low- or high-boiling petroleum ether. Examples of chlorinated aliphatic hydrocarbons which are suitable as solvents are chloroform, carbon tetrachloride or in particular ethylene dichloride. Examples of chlorinated aromatic hydrocarbons which are suitable as solvents are chlorobenzene and o-dichlorobenzene. Chlorobenzene is the preferred solvent. It is also possible to use mixtures of various solvents.

The amount of solvent used is normally 4 to 16 times, preferably 7 to 12 times, the amount of the compound used of formula II.

Examples of suitable catalysts are Friedel-Crafts catalysts known from the literature (compare George A. Olah, loc. cit., pages 8 to 13), namely metal halides, such as AlCl$_3$, FeCl$_3$, SbCl$_5$, SnCl$_4$, TiCl$_4$, BiCl$_3$, AlBr$_3$, FeBr$_3$, SbBr$_3$ or ZnBr$_2$, or acids, such as HClO$_4$, HOSO$_2$F, H$_3$PO$_4$, H$_3$PO$_3$ or H$_2$PO$_3$F. Free or polymer-bonded perfluoroalkanesulphonic acids having 1 to 10 C atoms in the perfluoroalkane chain, and also FeCl$_3$ and AlCl$_3$, are particularly suitable for the process according to the invention. AlCl$_3$ is very particularly preferred. The catalyst is used in an approximately molar quantity.

The reaction temperature depends strongly on the type of catalyst used. In the case of AlCl$_3$, the reaction is carried out at 10° to 70° C., the reaction being started at a low temperature and then continued at a higher temperature. In the case of FeCl$_3$ or free or polymer-bonded perfluoroalkanesulphonic acids, the temperature range is 50° to 140° C.

There are 4 possible ways of reacting the three reactants, i.e. a compound of the formula II, a catalyst and a p-nitrobenzoyl halide, in a solvent by the process according to the invention:

1. Solvent+catalyst+acid halide are initially introduced, and the compound of the formula II is then added.
2. Solvent+catalyst+compound of the formula II are initially introduced, and the acid halide is then added.
3. Solvent+acid halide+compound of the formula II are initially introduced, and the catalyst is then added.
4. Solvent+catalyst are initially introduced, and the acid halide+compound of the formula II are then added.

The 3rd and 4th possibilities are preferred, the 4th possibility being particularly preferred. When using the 4th possibility, it is advantageous to dilute the mixture of acid halide and compound of the formula II with a solvent in order to obtain a readily meterable, liquid mixture and in order to be able to control the reaction better.

Compounds of the formula II can be converted by known reduction processes, such as by means of hydrogen, in the presence of catalysts, if appropriate under pressure, or by means of iron or NaHS, into the corresponding amines of the formula III

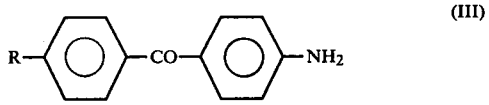

(III)

These represent organic intermediate products which are suitable for the preparation of pharmaceuticals and plant protection agents, but in particular for the preparation of dyestuffs. Amines of the formula III can be used particularly preferably to prepare, for example in a manner which is in itself known, by diazotisation and coupling, water-insoluble dyestuffs of the formula IV

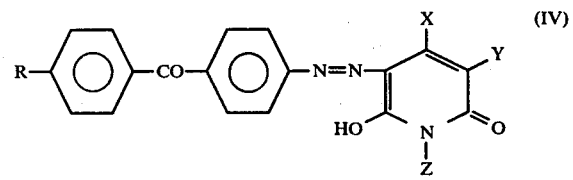

(IV)

wherein R has the abovementioned meaning and X denotes hydrogen, phenyl, or alkyl having 1 to 6 C atoms which can also be substituted by halogen or phenyl, Y denotes cyano, nitro, alkylcarbonyl having 1 to 3 C atoms in the alkyl radical, alkoxycarbonyl having 1 to 4 C atoms in the alkoxy radical, aminocarbonyl, the amino group of which can also be monosubstituted by phenyl or monosubstituted or disubstituted by alkyl having 1 to 4 C atoms, aminosulphonyl the amino group of which can also be monosubstituted by phenyl or monosubstituted or disubstituted by alkyl having 1 to 4 C atoms, phenylsulphonyl or alkylsulphonyl having 1 to 4 C atoms in the alkyl radicals, and Z denotes hydrogen, alkyl having 1 to 10 C atoms which can also be interrupted one or more times by oxygen and/or can also be substituted by phenyl, phenoxy, halogen, or hydroxyl, alkenyl having 2 to 7 C atoms which can also be substituted by phenyl, halogen, hydroxyl or alkoxy having 1 to 4 C atoms, cycloalkyl having 5 to 7 C atoms or phenyl.

Dyestuffs of the type mentioned have been described, for example, in German Offenlegungsschrift No. 1,813,385 and German Offenlegungsschrift No. 2,001,821. These dyestuffs are highly suitable for dyeing and printing synthetic, hydrophobic fibre materials, preferably of polyester, and mixtures of cellulose fibres with synthetic, organic fibres, by exhaust, thermosol and printing processes.

4-Isopropyl-4'-nitrobenzophenone and compounds of the formula I can be obtained by means of the present invention in a simple manner without elaborate purification operations in high purity and in yields up to about 95% of theory.

Unless otherwise indicated, parts denote parts by weight in the examples below.

EXAMPLE 1

710 parts of chlorobenzene and 160 parts of $AlCl_3$ are initially introduced. A mixture of 120 parts of cumene, 185.6 parts of p-nitrobenzoyl chloride and 410 parts of chlorobenzene is added dropwise in the course of 1 hour at 20° to 25° C., HCl gas being liberated. The mixture is then heated in the course of 1 hour to 60° C. and stirred for 1 hour at 60° C., 1,400 parts of ice are added, the aqueous phase is separated off in a separating funnel and the organic phase is concentrated in vacuo. 247.6 parts of 4-isopropyl-4'-nitrobenzophenone having a melting point of 95° C. are obtained. Yield: 92% of theory.

The reduction of 4-isopropyl-4'-nitrobenzophenone can be carried out, for example, as follows:

800 parts of water, 250 parts of iron chips and 28 parts of acetic acid are initially introduced, and the mixture is heated to 95° C. and stirred for 1 hour at 95° C. It is then cooled to 90° C., 800 parts of ethanol are added, and 55 parts of 4-isopropyl-4'-nitrobenzophenone are added in a solid form in small portions in the course of 30 minutes. The mixture is heated for 8 hours under reflux, its pH is adjusted to 9 by means of 44 parts of sodium carbonate solution, 600 parts of ethanol are added, heating under reflux is carried out for 15 hours, the mixture is filtered hot and the residue is washed three times with 200 parts each of hot ethanol. Ethanol is distilled off from the combined filtrates and the aqueous bottom is cooled down. The precipitated crystals are then filtered off and dried in vacuo. 45.5 parts of 4-isopropyl-4'-aminobenzophenone having a melting point of 110° C. are obtained. The valuable dyestuff of the formula VI

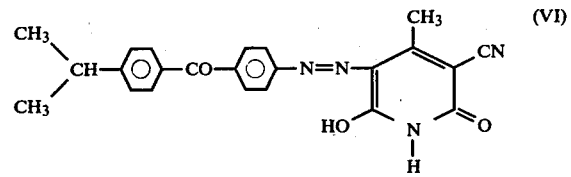

(VI)

can be prepared from 4-isopropyl-4'-aminobenzophenone as indicated in German Offenlegungsschrift No. 2,001,821, Table 1, Example 15.

EXAMPLE 2

1,100 parts of chlorobenzene, 120 parts of cumene and 185.6 parts of p-nitrobenzoyl chloride are initially introduced. 160 g of $AlCl_3$ are added in the course of 1 hour at 20° to 25° C., the evolution of HCl commencing. If the further procedure followed is as indicated in Example 1, 246 parts of 4-isopropyl-4'-nitrobenzophenone are obtained. Yield: 91.4% of theory.

EXAMPLE 3

1,200 parts of ethylene chloride, 120 parts of cumene and 185 parts of p-nitrobenzoyl chloride are initially introduced and 160 g of AlCl$_3$ are added in the course of 1 hour at 25° to 30° C. If the remaining procedure followed is as indicated in Example 1, 226 parts of 4-isopropyl-4'-nitrobenzophenone are obtained. Yield: 84% of theory.

EXAMPLE 4

1,100 parts of chlorobenzene, 134.2 parts of tert.-butylbenzene and 185.6 parts of p-nitrobenzoyl chloride are initially introduced and 160 g of AlCl$_3$ are added in the course of 1 hour at 20° to 25° C. If the remaining procedure followed is as indicated in Example 1, 269 parts of 4-tert.-butyl-4'-nitrobenzophenone having a melting point of 108° to 110° C. (literature: 112° to 113° C.) are obtained. Yield: 95% of theory.

If the further procedure followed is as indicated in Example 1, it is possible to prepare the dyestuff of the formula VII

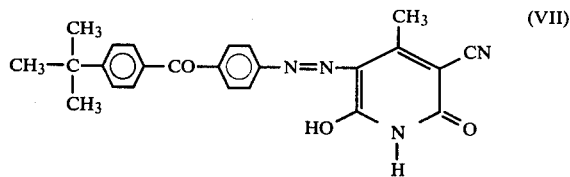

which dyes hydrophobic fibre material, preferably polyethylene glycol terephthalate or mixtures containing this polyester, in a yellow shade having a high colour strength. The dyeings have outstanding coloristic properties, such as light-fastness, fastness to heat setting, pH stability, good levelling capacity and they are resistant to thermomigration.

What is claimed is:
1. 4-Isopropyl-4'-nitrobenzophenone.

* * * * *